United States Patent [19]

Wieringa

[11] Patent Number: 4,977,158
[45] Date of Patent: Dec. 11, 1990

[54] DIBENZOXEPINON AND DIBENZOTHIEPINO-PYRIDINOL OR -PYRROTOL DERIVATIVES WITH ANTI-DEPRESSANT ACTION

[75] Inventor: Johannes H. Wieringa, Heesch, Netherlands

[73] Assignee: Akzo N.V., Arnhem, Netherlands

[21] Appl. No.: 397,228

[22] Filed: Aug. 23, 1989

[30] Foreign Application Priority Data

Aug. 26, 1988 [NL] Netherlands .................. 8802109

[51] Int. Cl.$^5$ .................. A61K 31/40; A61K 31/44; C07D 491/044
[52] U.S. Cl. .................. 514/285; 514/410; 546/62; 548/421; 548/423
[58] Field of Search .................. 546/62; 548/421, 423, 548/422; 514/410, 285

[56] References Cited

U.S. PATENT DOCUMENTS

| | | | |
|---|---|---|---|
| 4,145,434 | 3/1979 | van der Burg | 548/421 |
| 4,154,836 | 5/1979 | van der Burg | 546/62 |
| 4,158,058 | 6/1979 | van der Burg | 546/62 |
| 4,271,177 | 6/1981 | van der Burg | 514/410 |
| 4,271,179 | 6/1981 | van der Burg | 514/410 |

Primary Examiner—Mukund J. Shah
Assistant Examiner—Edward C. Ward
Attorney, Agent, or Firm—William M. Blackstone; Donna Bobrowicz

[57] ABSTRACT

The invention relates to novel tetracyclic compounds with an anti-depressant action, without neuroleptic or sedative side effects, of the general formula I

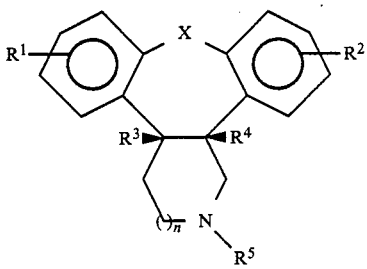

and also functional derivatives hereof, wherein:

$R^1$ represents one or two identical or different substituents denoting H, OH, halogen, $C_1$–$C_4$ alkyl or $C_1$–$C_4$ alkoxy;

$R^2$ represents one or two identical or different substituents having the same meaning as $R^1$;

$R^3$ and $R^4$ are two substituents which are in the cis configuration and of which one is H and the other is OH;

$R^5$ is H or $C_1$–$C_4$ alkyl;

X denotes O or S;

n is 0 or 1.

5 Claims, No Drawings

DIBENZOXEPINON AND DIBENZOTHIEPINO-PYRIDINOL OR -PYRROTOL DERIVATIVES WITH ANTI-DEPRESSANT ACTION

The invention relates to novel tetracyclic compounds of the general formula I:

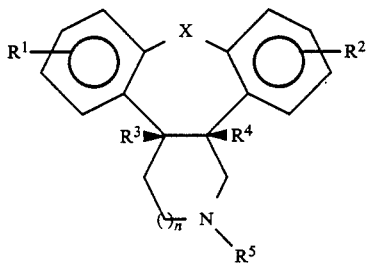

and also functional derivatives hereof, wherein:

$R^1$ represents one or two identical or different substituents denoting H, OH, halogen, $C_1$–$C_4$ alkyl or $C_1$–$C_4$ alkoxy;

$R^2$ represents one or two identical or different substituents having the same meaning as $R^1$;

$R^3$ and $R^4$ are two substituents which are in the cis configuration and of which one is H and the other is OH;

$R^5$ is H or $C_1$–$C_4$ alkyl;

X denotes O or S;

n is 0 or 1.

The compounds according to the invention have an interesting anti-depressant action, surprisingly without exhibiting neuroleptic or sedative properties.

In this respect these novel compounds differ from known related compounds, such as described, for example, in British Patent No. 1,567,862, and they are very useful for combating depressive conditions without the patient being hindered by sedative side effects. Moreover, the compounds of the invention can be used in combating anxiety conditions, such as agoraphobia.

The compounds of the general formula II, wherein $R^1$, $R^2$, $R^5$ and n have the same meaning as above,:

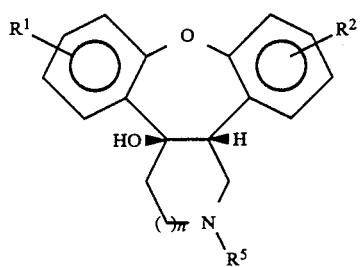

and the functional derivatives hereof are considered to be some of the most active compounds. Compounds III and IV and their functional derivatives may be mentioned in particular.

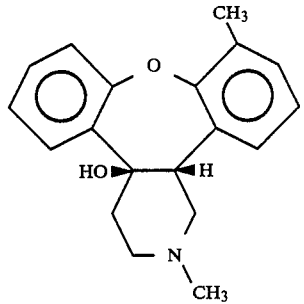

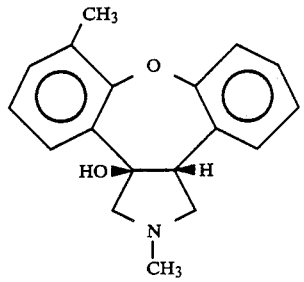

In the definition of compounds of the general formula I $C_1$–$C_4$ alkyl denotes saturated alkyl substituents having 1 to 4 carbon atoms, specifically methyl, ethyl, propyl, isopropyl, butyl, sec-butyl, isobutyl and tert-butyl. $C_1$–$C_4$ alkoxy denotes alkoxy substituents having 1 to 4 carbon atoms, in which the alkyl group has the above meaning.

Functional derivatives of compounds of the general formula I are to be understood as meaning:

nitrogen oxides;

pharmaceutically acceptable salts;

O-acyl ($C_1$–$C_{20}$) esters; and quaternary ammonium derivatives.

O-acyl ($C_1$–$C_{20}$) esters are esters derived from saturated and unsaturated aliphatic carboxylic acids having 1 to 20 carbon atoms, such as acetic acid, propionic acid, octanecarboxylic acid, dodecanecarboxylic acid, palmitic acid, palmitolinic acid, stearic acid, linoleic acid and the like.

Salts of the compounds of the general formula I are understood as meaning acid addition salts which are derived from pharmaceutically acceptable inorganic and organic acids. Customary acids are hydrochloric acid, sulphuric acid, phosphoric acid, acetic acid, propionic acid, maleic acid, fumaric acid, malonic acid, tartaric acid, citric acid, ascorbic acid, salicylic acid, benzoic acid and the like.

The compounds according to the invention can be prepared in a manner customary for analogous compounds.

A suitable synthesis for compounds of the general formula I wherein $R^3$ is OH and $R^4$ is H comprises the condensation reaction of compounds of the general formula V:

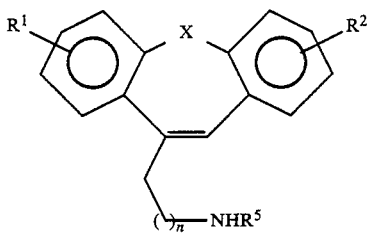

V or a salt hereof, wherein $R^1$, $R^2$, $R^5$, n and X have the meaning indicated above, with formaldehyde or a source of formaldehyde, such as paraformaldehyde, in a suitable solvent. The reaction is carried out at the reflux temperature of the particular solvent, but lower temperatures down to room temperature are very possible. The reaction is accelerated by the addition of a catalyst, as which, inter alia, phosphoric acid, polyphosphoric acid, hydrochloric acid and sulphuric acid are used. The reaction can proceed directly or via an intermediate iminium salt.

The starting materials for formula V compounds are described in the literature.

Another method of preparation with which compounds of the general formula I are obtained in which $R^3$ is H and $R^4$ is OH starts from compounds of the general formula VI:

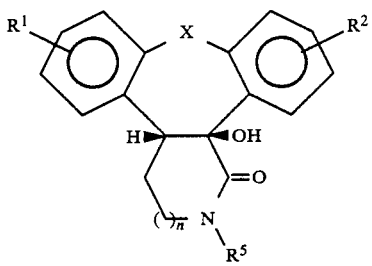

VI wherein $R^1$, $R^2$, $R^5$, x and n have the meaning given above, which can be converted by means of reduction into compounds of the general formula I ($R^3$ is H; $R^4$ is OH). Suitable reductants are all reagents which can be used for the reduction of amide bonds, for example metal hydrides such as $LiAlH_4$, $LiAlH_4$—$AlCl_3$ mixtures and $NaBH_4$ in suitable solvents, such as ether or tetrahydrofuran, and ethanol in the case of $NaBH_4$.

Compounds of the general formula VI can, in turn, be prepared by oxidation of compounds of the general formula VII:

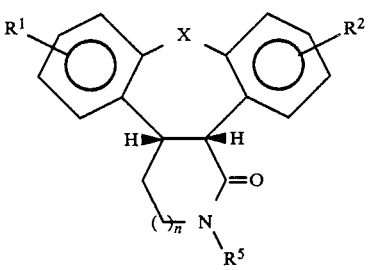

VII wherein $R^1$, $R^2$, $R^5$, x and n have the meaning indicated above. Compounds of the formula VII are known, for example in the previously mentioned British Patent No. 1,567,862.

Compounds of general formula I wherein $R^5$ is H can be converted to compounds of the formula I wherein $R^5$ is $C_1$-$C_4$ alkyl. A conversion of this type is obtained by alkylation of the starting material (the cyclic amine), for example by reaction with an alkyl halide or by means of a reductive alkylation of a Schiff base.

The methods of preparation as described above in general yield mixtures of the cis and trans compounds, that is to say compounds of the general formula I which fall under the scope of the invention and compounds in which the groups $R^3$ and $R^4$ are in the trans position relative to one another. The latter compounds do not fall under the scope of the invention and must be removed, for example by crystallization or chromatography.

The compounds of the formula I are usually obtained as the racemate. If desired, this racemate can be split into its enantiomers in the conventional way with the aid of an optically active acid. Both enantiomers, but also mixtures thereof, are considered part of the invention. By using optically pure starting materials it is also possible to obtain one of the enantiomers.

The nitrogen oxides of the compounds of the general formula I are obtained by oxidation of the free base I with the aid of hydrogen peroxide or a per-acid.

The quaternary ammonium derivatives of the compounds of the general formula I are obtained by reaction of amines of formula I with suitable reagents, such as methyl iodide, ethyl bromide and the like, in a manner known in the art.

The O-acyl esters of the compounds of the general formula I are obtained by allowing these compounds to react with an acid, acid chloride or active ester of the acid, in suitable solvents and if necessary catalysed by mineral acids or organic acids, such as p-toluenesulphonic acid. Esterification procedures of this type are generally known in organic chemistry.

These esters frequently display a better resorption, so that the biological availability is increased. In this connection the higher esters are of particular importance because of their favourable lipophilic properties.

The compounds according to the invention can be processed to pharmaceutical preparations for enteral or parenteral administration by mixing with suitable auxiliaries. Possible forms of administration are oral, local and parenteral, for example in the form of a tablet, pill, powder, capsule, solution, emulsion, suspension, paste, spray or suppository. The oral administration form will usually be preferred for out-patients; for patients in the hospital, administration by means of injections will be widely used in addition.

The daily dosage is preferably 0.01-20 mg per kg body weight. For administration to humans a dosage of 10 to 700 mg per day and in particular 25-500 mg per day is preferred.

The following examples serve to illustrate the invention.

EXAMPLE 1 cis-1,2,3,4,4a,13b-hexahydro-2,10-dimethyldibenz [2,3:6,7]oxepino[4.5-c]pyridin-4a-ol 59 g 1,N-dimethyl-dibenz[b,f]oxepin-5-ethanamine were dissolved in 200 ml 96% alcohol under a nitrogen atmosphere. While stirring, 2 1 2N HCl were added, followed by 880 ml of a 37% formaldehyde solution.

This mixture was stirred for 40 hours at 50° C. After cooling to 20° C., the aqueous layer was removed and the precipitated solid substance was dissolved in 200 ml methylene chloride. The aqueous layer was extracted with 2×800 ml ether and the combined organic solutions washed with 2×650 ml 1N HCl. The acid extracts were collected and brought to pH 10 with 25% aqueous ammonia. After stirring for 10 minutes, 2 l methylene chloride were added. The mixture was stirred for a further 10 minutes, after which the layers were separated and the aqueous layer was extracted with 2×600 ml methylene chloride. This extract was dried over sodium sulphate and evaporated to 700 ml under vacuum. After cooling to 20° C., the mixture was stirred for 5 hours, after which the precipitated crystals were collected and washed with methylene chloride. The mother liquor was concentrated to 200 ml and stirred for 2 hours at 15° C. The second amount of crystals was collected and washed with cold methylene chloride. The total yield was 70 g (63%).

By recrystallization from methylene chloride material of sufficient purity was obtained. m.p. 129° C.

EXAMPLE 2

The following compounds were prepared in a manner analogous to that described in Example 1:
cis-1,2,3,4,4a,13b-hexahydro-2-methyldibenz[2,3:6,-7]oxepino[4,5-c]pyridin-4a-ol. m.p. 168° C.
cis-1,2,3,4,4a,13b-hexahydro-10-methyldibenz[2,3:6,-7]oxepino[4,5-c]pyridin-4a-ol. m.p. 185° C.
cis-12-chloro-1,2,3,4,4a,13b-hexahydro-2-methyldibenz[2,3:6,7]oxepino[4,5-c]pyridin-4a-ol (Z)-2-butenedioate (1:1). m.p. 206° C.
cis-11-chloro-1,2,3,4,4a,13b-hexahydro-2-methyldibenz[2,3:6,7]oxepino[4,5-c]pyridin-4a-ol (Z)-2-butenedioate (1:1). m.p. 194° C.
cis-8-chloro-1,2,3,4,4a,13b-hexahydro-2-methyldibenz[2,3:6,7]oxepino[4,5-c]pyridin-4a-ol (Z)-2-butenedioate (1:1). m.p. 181° C.
cis-2,3,3a,12b-tetrahydro-2,7-dimethyl-1H-dibenz[2,3:6,7]oxepino[4,5-c]pyrrol-3a-ol (Z)-2-butenedioate (1:1). m.p. 163° C.

EXAMPLE 3 cis-2,3,3a,12b-tetrahydro-2,7-dimethyl-1H-dibenz[2,3:6,7]oxepino[4,5-c]pyrrol-3a-ol (Z)-2-butenedioate (1:1).

(a) A solution of 46 g of a cis-trans mixture of 2,3,3a,12b-tetrahydro-2,9-dimethyl-1H-dibenz[2,3:6,-7]oxepino[4,5-c]pyrrol-1-one in 1 l of 4:1 (v/v) mixture of DMSO (dimethylsulphoxide) and t-butanol was introduced into a 3 l reaction vessel. The solution was saturated with oxygen by passing in oxygen for 1 hour. The solution was cooled to 10° C. while passing in oxygen and 13.5 g sodium methoxide was added in portions. The cooling bath was removed and after 30 minutes a check was made to establish whether the reaction was complete. If necessary, oxygen was again fed in for 2 hours. The contents of the reaction vessel were poured out into 4 l water and the mixture acidified with dilute HCl. The mixture was extracted with methylene chloride and this extract was washed with water. The organic layer was dried over sodium sulphate, evaporated and taken up in 100 ml ethyl acetate. The residue dissolved completely after warming. The cis isomer then crystallized out and the mother liquor was chromatographed over silica with ethyl acetate. This gave a second portion of cis isomer. The total yield of cis isomer was 25.5 g.

(b) A suspension of 11 g LiAlH$_4$ in 800 ml ether was prepared in a 5 l reaction vessel. A solution of 22 g AlCl$_3$ in 800 ml of ether was then added, with cooling. The suspension obtained was cooled to about 5° C., after which the cis-2,3,3a,12b-tetrahydro-12b-hydroxy-2,9-dimethyl-1H-dibenz[2,3:6,7]oxepino[4,5-c]pyrrol-1-one (25.5 g), obtained in the previous step, dissolved in 650 ml THF (tetrahydrofuran) was added dropwise in the course of 1 hour. The temperature was kept at 5° C. during this addition. After the addition, the mixture was stirred for a further 1 hour, tlc was used to check whether the reaction was complete, and the reaction mixture was decomposed by the slow addition of 150 ml 1N NaOH. The mixture was stirred for a further 1 hour, after which the organic salts were filtered off and washed thoroughly with methylene chloride. The combined filtrates were evaporated and the residue was taken up in toluene/ethanol (8:1, v/v) and chromatographed over silica with this solvent mixture.

By recrystallization from a toluene/hexane mixture a pure product was obtained which was mixed with 6.1 g maleic acid. 20.6 g (65%) of the pure end product, m.p. 163° C., was obtained by crystallization from ethyl acetate.

EXAMPLE 4

The following compounds were prepared in a manner analogous to that described in Example 3.
cis-1,2,3,4,4a,13b-hexahydro-2-methyldibenz[2,3:6,-7]oxepino[4,5-c]pyridin-13b-ol. m.p. 162° C.
cis-11-chloro-1,2,3,4,4a,13b-hexahydro-2-methyldibenz[2,3:6,7]oxepino[4,5-c]pyridin-13b-ol hydrochloride. m.p. 242° C.
cis-6-chloro-1,2,3,4,4a,13b-hexahydro-2-methyldibenz[2,3:6,7]oxepino[4,5-c]pyridin-13b-ol. m.p. 134 ° C.
cis-1,2,3,4,4a,13b-hexahydro-2,10-dimethyldibenz[2,3:6,7]oxepino[4,5-c]pyridin-13b-ol (Z)-2-butenedioate (1:1). m.p. 174° C.
cis-1,2,3,4,4a,13b-hexahydro-2-methyldibenzo[2,3:6,7]thiepino[4,5-c]pyridin-13b-ol hydrochloride. m.p. 229° C.
cis-2,3,3a,12b-tetrahydro-2-methyl-1H-dibenz[2,3:6,-7]oxepino[4,5-c]pyrrol-3a-ol (E)-2-butenedioate (1:1). m.p. 178° C.
cis-5-chloro-2,3,3a,12b-tetrahydro-2-methyl-1H-dibenz[2,3:6,7]oxepino[4,5-c]pyrrol-3a-ol (Z)-2-butenedioate (1:1). m.p. 191° C.
cis-6-chloro-2,3,3a,12b-tetrahydro-2-methyl-1H-dibenz[2,3:6,7]oxepino[4,5-c]pyrrol-3a-ol hydrochloride. m.p. 201° C.
cis-2,3,3a,12b-tetrahydro-2-methyl-1H-dibenzo[2,3:6,7]thiepino[4,5-c]pyrrol-3a-ol hydrochloride.
cis-2,3,3a,12b-tetrahydro-2,7-dimethyl-1H-dibenz[2,3:6,7]oxepino[4,5-c]pyrrol-3a-ol (Z)-2-butenedioate (1:1). m.p. 163° C.

EXAMPLE 5 cis-1,2 3,4,4a,13b-hexahydro-2,10-dimethyldibenz[2,3:6,7]oxepino[4,5-c]pyridin-13b-ol (Z)-2-butenedioate (1:1).

(a) A solution of 8.6 g cis-1,2,3,4,4a,13b-hexahydro-13b-hydroxy-2,10-dimethyldibenz[2,3:6,7]oxepino[4,5-c]pyridin-1-one in 550 ml THF was introduced into a 1 l reaction vessel. 6 g LiAlH$_4$ were added, while stirring, and after 1.5 hours the mixture was decomposed by adding 24 ml water. The mixture was stirred for 1 hour and the salts were filtered off and washed with THF. After evaporating the combined THF solutions, the mass was taken up in 200 ml ether and the solid substance (a dimer compound) filtered off with suction.

(b) The solid substance was suspended in 200 ml ethanol (96%) and HCl gas was passed in for 10 minutes. The mixture was brought to the reflux temperature, the solid substance slowly going into solution. The solution was stirred for a further 15 minutes, after which the mixture was evaporated to dryness under vacuum, the crude quaternary iminium salt being obtained.

(c) 1 g of the quaternary iminium salt was dissolved as well as possible in 25 ml absolute ethanol, with heating. The mixture was cooled to room temperature and 1.5 g NaBH$_4$ was added. After the exothermic reaction had ceased, the mixture was stirred for a further 2 hours under a nitrogen atmosphere at room temperature. 15 ml methanol were then added and the reaction mixture was refluxed for 30 minutes. The mixture was evaporated to dryness and the residue taken up in 100 ml toluene and washed with water. The extract was dried over sodium sulphate and evaporated to dryness. The maleate was prepared in the manner described in example 3. m.p. 174° C.

EXAMPLE 6

The following compounds were prepared in a manner analogous to that described in Example 5:
cis-2,3,3a,12b-tetrahydro-2-methyl-1H-dibenz[2,3:6,-7]oxepino[4,5-c]pyrrol-3a-ol (E)-2-butenedioate (1:1). m.p. 178° C.
cis-5-chloro-2,3,3a,12b-tetrahydro-2-methyl-1H-dibenz [2,3:6,7]oxepino[4,5-c]pyrrol-3a-ol (Z)-2-butenedioate (1:1). m.p. 191° C.

EXAMPLE 7

Enantiomeric separation of racemic cis-2,3,3a,12b-tetrahydro-2-methyl-1H-dibenz[2,3:6,7]oxepino[4,5-c]pyrrol-3a-ol.

150 g of racemic cis-2,3,3a,12b-tetrahydro-2-methyl-1H-dibenz[2,3:6,7]oxepino[4,5-c]pyrrol-3a-ol was dissolved in 3 l 96% ethanol, after which 106 g (−) dibenzoyltartaric acid [(−)DBT] was added. After 5 days the crystals were filtered off with suction The mother liquor was again crystallized with (−) DBT and this was repeated twice. The collected crystals were washed free with 33% NaOH and methylene chloride, after which the crystals were recrystallized from ethyl acetate. The mother liquor was again crystallized from (−) DBT and the crystals rendered free and recrystallized from ethyl acetate and then from hexane. This gave 4.8 g (−)-cis-2,3,3a,12b-tetrahydro-2-methyl-1H-benz [2,3:6,7]oxepino[4,5-c]pyrrol-3a-ol: $[\alpha]^{20}_D = -103°$ (c=0.5, CH$_2$Cl$_2$), m.p. 113.5° C.

The collected mother liquors and unprocessed crystalline material were rendered free and then treated in the same way as described above with (+)-dibenzoyltartaric acid. 6.5 g (+)-cis-2,3,3a,12b-tetrahydro-2-methyl-1H-benz[2,3:6,7]oxepino [4,5-c]pyrrol-3a-ol were obtained: $[\alpha]^{20}_D = +101°$ (c=0.5, CH$_2$Cl$_2$), m.p. 114° C.

EXAMPLE 8 cis-1,2,3,4,4a,13b-hexahydro-2,10-dimethyldibenz [2,3:6,7]oxeoino[4,5-c]pyridin-4a-ol acetate (ester)

While stirring, 2.05 g triethylamine were added to 5 g of the compound from Example 1 in 50 ml dry dimethylformamide under nitrogen. 1.32 ml acetyl chloride in 5 ml dry dimethylformamide were then added, the temperature rising to 35° C. The suspension was stirred for a further 48 hours at room temperature, after which the reaction was brought to completion by adding an extra amount of 0.2 ml acetyl chloride and 0.2 ml triethylamine. After stirring for a further 4 hours, the mixture was poured out into water and extracted with ether and the organic layer was washed with water and evaporated. The crude product was recrystallized from ethanol, after which a second amount of substance was obtained from the mother liquor after column chromatography over silica (toluene-ethanol 9:1). The collected fractions were recrystallized from ethanol, after which 2.15 g cis-1,2,3,4,4a,13b-hexahydro-2,10-dimethylbenz[2,3:6,-7]oxepino[4,5-c]pyridin-4a-ol acetate (ester) were obtained. m.p. 160° C.

EXAMPLE 9

The following compounds were prepared in a manner analogous to that described in example 8:
cis-1,2,3,4,4a,13b-hexahydro-2-methyldibenz[2,3:6,-7]oxepino[4,5-c]pyridin-4a-ol acetate (ester). m.p. 128° C.
cis-1,2,3,4,4a,13b-hexahydro-2,10-dimethyldibenz [2,3:6,7]oxepino[4,5-c]pyridin-4a-ol hexadecanoate (ester). m.p. 68° C.
cis-6-chloro-2,3,3a,12b-tetrahydro-2-methyl-1H-dibenz [2,3:6,7]oxepino[4,5-c]pyrrol-3a-ol acetate (ester). m.p. 151° C.
cis-2,3,3a,12b-tetrahydro-2-methyl-1H-dibenz [2,3:6,7]oxepino[4,5-c]pyrrol-3a-ol acetate (ester). m.p. 123° C.

EXAMPLE 10 cis-1,2,3,4,4a,13b-hexahydro-4a-hydroxy-2,2,10-trimethyldibenzo[2,3:6,7]oxepino[4,5-c]pyridinium iodide 5.0 g (17 mmol) of the compound of Example 1 were dissolved in a mixture of 200 ml of toluene, 100 ml of ether and 50 ml of methanol. While stirring 50 ml of methyl iodide were added at room temperature. After 24 hrs crystals had formed. The mother liquor was filtered off and the crystals collected. This gave 6.75 g (91%) of the quaternary iodide. m.p. >260° C. (dec.).

EXAMPLE 11

(2α,4aα,13bα)-1,2,3,4,4a,13b-hexahydro-2,10-dimethyldibenzo [2,3:6,7[oxepino[4.5-c]pyridin-4a-ol N-oxide 8.43 g (28.6 mmol) of the compound of Example 1 were dissolved in 300 ml of methylene chloride and cooled to 0° C. while stirring. A solution of 10 g of m-chloroperbenzoic acid in 100 ml of methylene chloride was then added in 2 hrs. After 2.5 hrs the reaction was complete. The excess of oxidant was destroyed by slow addition of saturated sodium sulphite solution (100 ml). Next 200 ml of 2N sodium hydroxide solution was added and the solution concentrated to dryness. The residue was dissolved in hot ethanol as far as possible. The remaining salts were removed by filtration and the filtrate was again concentrated to dryness. Now the residue was refluxed with excess of methylene chloride and again filtered with suction. The methylene chloride layer was concentrated to dryness and the residue recyrstallized from acetone, yielding 6.75 g (76%) of fine crystals. m.p. 213° C.

I claim:

1. Tetracyclic compounds of the formula I:

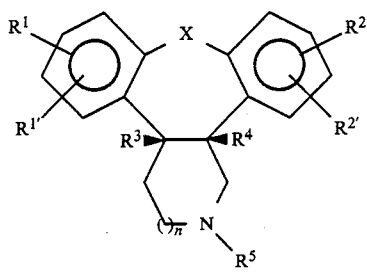

wherein:
R$^1$R$^{11}$, R$^2$ and R$^{21}$ independently represent substitutents selected from the group consisting of H, OH, halogen, C$_1$-C$_4$ alkyl and C$_1$-C$_4$ alkoxy;
R$^3$ and R$^4$ are two substituents which are in the cis configuration and of which one is H and the other is OH;
R$^5$ is H or C$_1$-C$_4$ alkyl;
X denotes O or S;
n is 0 or 1;
and functional derivatives hereof.

2. Compounds according to claim 1, wherein X is O.

3. Compounds according to claim 1, of the formula III:

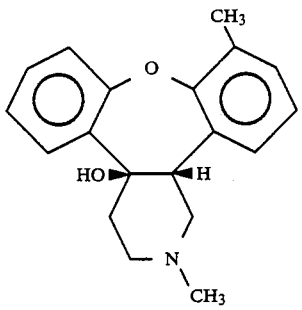

4. Compounds according to claim 1, of the formula IV:

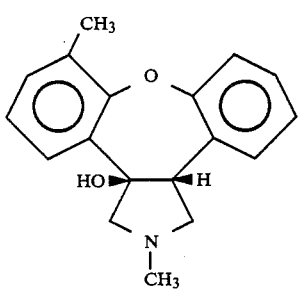

5. A pharmaceutical preparation having anti-depressant action in humans comprising at least one compound according to claim 1, and a pharmaceutically acceptable carrier.

* * * * *

UNITED STATES PATENT AND TRADEMARK OFFICE
CERTIFICATE OF CORRECTION

PATENT NO. : 4,977,158
DATED : December 11, 1990
INVENTOR(S) : Johannes H. Wieringa It is certified that error appears in the above-identified patent and that said Letters Patent is hereby corrected as shown below:

Title page: Item (54) and column 1:

"DIBENZOXEPINON AND DIBENZOTHIEPINO-PYRIDINOL OR - PYRROTOL DERIVATIVES WITH ANTI-DEPRESSANT ACTION" should read -- DIBENZOXEPINO- AND DIBENZOTHIEPINO-PYRIDINOL OR -PYRROLOL DERIVATIVES WITH ANTI-DEPRESSANT ACTION --.

In claim 1, line 18, after $R^1$, delete "$R^{11}$" and replace with -- ,$R^{1'}$ --.

In claim 1, line 18, after and, delete "$R^{21}$" and replace with -- $R^{2'}$ --.

Signed and Sealed this

Fourth Day of August, 1992

Attest:

DOUGLAS B. COMER

Attesting Officer

Acting Commissioner of Patents and Trademarks